United States Patent [19]

Lowder et al.

[11] Patent Number: 5,094,839
[45] Date of Patent: Mar. 10, 1992

[54] ABRASIVE POLISHING COMPOSITION

[75] Inventors: James T. Lowder, Columbus, Ohio; John P. McDermott, Wheeling, Ill.; Mark E. Watkins, Columbus, Ohio

[73] Assignee: Abrasive Technology, Inc., Westerville, Ohio

[21] Appl. No.: 611,991

[22] Filed: Nov. 9, 1990

[51] Int. Cl.$^5$ .................... A61K 6/00; A61C 17/00
[52] U.S. Cl. .................................... 424/49; 433/216
[58] Field of Search ............... 424/195.1, 49; 433/216

[56] References Cited

U.S. PATENT DOCUMENTS

| | | | |
|---|---|---|---|
| 4,021,263 | 5/1977 | Rosenblum | 106/288 B |
| 4,344,931 | 8/1982 | Aguilar | 424/52 |
| 4,349,533 | 9/1982 | Dent | 424/52 |
| 4,435,160 | 3/1984 | Randklev | 433/9 |
| 4,648,845 | 3/1987 | Orlowski | 433/217.1 |
| 4,664,906 | 5/1987 | Sidos | 424/49 |
| 4,954,082 | 9/1990 | Weissman | 433/80 |

OTHER PUBLICATIONS

Kirk-Othmer Encyclopedia of Chemical Technology 3rd Ed. vol. 1, 1978, p. 31, vol. 7, pp. 514–515.
The Merck Index 11th Ed. 1989 Merck & Co., Rahway, N.J., pp. 2959, 4384, 4493, 4494, 176, 1868, 1878, 232, 6022, 7871, Primary Examiner—Ronald W. Griffin
Assistant Examiner—Ralph Gitomer
Attorney, Agent, or Firm—Francis T. Kremblas, Jr.

[57] ABSTRACT

A polishing composition carrying abrasive particles having a carrier vehicle comprising an organic liquid vehicle, such as glycerine, a mixture of gelling agents comprising an edible gum and a seaweed extract, and water in a ratio which forms a relatively viscous semi-gel or sol. The preferred gelling agent mixture is gum tragacanth and agar which provides the carrier vehicle with physical properties improving its ability to cling to the rotary applicators and the work surface during use as a polishing agent. The preferred compositions include greater than about 85 percent by weight of glycerine and less than about 10 percent by weight of water and exhibit Newtonian or near Newtonian flow characteristics and resists apparent melting at temperatures generated during use. Also disclosed is a method of using such a composition in a multiple step sequence using a reduction in abrasive particle size in each polishing step to achieve a smooth, mirror-like finish, particularly useful with certain types of restorative tooth materials.

11 Claims, No Drawings

ABRASIVE POLISHING COMPOSITION

BACKGROUND ART

Compositions used for fine polishing applications generally are relatively old and well-known, such as the oil soluble pastes, oils and waxes. Some compositions, particularly those useful in the dental field, employ a humectant such as glycerine, polyglycols and other known humectants with water to form a liquid vehicle. Gelling agents are also employed to provide thickness and include natural and synthetic gums and gum-like materials. It is also known that such compositions should include known preservatives to reduce bacterial attack of the composition and provide extended shelf life.

In dental polishing compositions, such as disclosed in prior U.S. Pat. Nos. 4,702,905; 4,528,180, 4,705,680 and 4,814,160, combinations of such ingredients are disclosed and are directed to dental creams, pastes and gels which incorporate the well-known cleaning or polishing components such as water-insoluble alkaline earth metal salts or similar agents.

These polishing compositions are useful and satisfactory for manual brushing of teeth. However, they are not satisfactory for polishing applications wherein rotary applicators are employed to obtain very fine, highly reflective mirror-like surfaces because of the type of abrasive incorporated therein. Diamond or other equivalent hard abrasives are typically necessary to accomplish a higher degree of polishing as opposed to mere cleaning of such surfaces to provide a smooth, mirror-like finish.

Presently available dental diamond polishing compositions incorporate a carrier vehicle for the diamond particles which appear to have very similar physical properties to the typical manual brushing compositions forming a creamy mass, gel or paste. Such diamond polishing compositions exhibit less than wholly satisfactory physical properties related to adherence to the applicators and/or the tooth surface during use and the ability to retain a relatively viscous character during polishing.

To obtain the desired smooth, mirror-like finish, in an acceptable manner requires using rotating applicators which may generate high shear forces and significantly increased temperatures. Under these rigorous conditions, a significant amount of the prior art compositions tend to be spun off during use. Such spin off or spattering is due to one or a combination of the following deficiencies; the intrinsic lack of sufficient adherence to the applicator or the work surface; a significant decrease in apparent viscosity due to friction caused increase in temperature which appears to be a form of melting; or a decrease in viscosity due to shear forces generated during use. This decrease in viscosity due to shear forces is common to prior art gels or pastes incorporating unidentified gums and gum-like materials and is a psuedoplastic or thixotropic flow property.

The loss of the composition by spinning off during use represents inefficient use of the abrasive particles dispersed in the carrier. The lack of sufficient adherence of the composition to the applicator and the work surface being polished also tends to diminish the effectiveness of the polishing action upon the work surface. Attempts to overcome such deficiencies in prior art polishing compositions included overloading of the composition with the abrasive agent. This is particularly uneconomical when the more expensive abrasive materials are employed and does not always yield the intended result.

Additionally, spin off of the composition during use is distracting and excessive spattering of the composition, particularly in dental "chairside" applications, is inconvenient and generally undesirable to the user and the patient.

While many presently available "diamond polishing and glazing" formulations have a consistency which permits the product to be dispensed from a syringe-type package or a squeeze tube, at least one is packaged in a semi-hard paste form somewhat like conventional shoe polish or the like.

Those skilled in this art have failed to develop a carrier agent possessing improved physical properties related to providing more efficient and effective use of the abrasive which is also convenient to manufacture, package or provide and use.

There is a need for an abrasive polishing composition having an improved balance of physical properties wherein the vehicle carrying the abrasive adheres well to the applicator and to the work surface, as well as to itself, and also possesses Newtonian or near Newtonian flow characteristics wherein viscosity is not significantly reduced by shear forces. Further the polishing composition should resist a decrease in viscosity due to the build up of heat during typical applications which can significantly reduce adherence of the composition to the applicator and work surface.

SUMMARY OF THE INVENTION

The present invention relates generally to abrasive containing polishing compositions and particularly to those employing diamond or other hard abrasive particles for achieving a high grade, mirror-like surface using relatively high speed applicators. More particularly, a polishing composition suitable for dental laboratory and intra-oral applications for providing a glazed or highly polished finish to teeth and tooth restorations as well as being suitable for industrial applications is disclosed which exhibits improved properties for more efficient and effective polishing action.

It should be noted that the rotary applicators used to perform the mirror-like polished surfaces referred to herein rotate at speeds in the typical range of 200 to 20,000 rpm's for example. Therefore significant centrifugal forces and heat generation may be encountered during this process.

The vehicle carrying the abrasive particles of a preferred polishing composition according to the present invention includes glycerine as a humectant, gelling agents in the form of a mixture of gum tragacanth and agar, and a relatively small amount of water. More particularly, the ratio of the gelling agents employed provides a viscous semi-gel or sol type mixture which possesses improved properties related to viscosity and adherence to the applicator, the surface being polished and to itself. These factors are important to obtain more effective and efficient use of the abrasive particles.

Additionally, such a composition must also be economical to package for convenient dispensing and use. In dental applications, the components must be suitable for use in the human oral cavity. Shelf life and resistance to bacterial growth are other important factors which must meet high standards for commercial acceptance.

In accordance with the present invention, it has been found that a semi-gel or sol which exhibits Newtonian or near Newtonian flow characteristics, rather than the more typical psuedoplastic characteristics, demonstrates improved efficiency. Further the composition must adhere well to the applicator and substrate, as well as itself, to provide improved efficiency and effectiveness of the abrasive particles dispersed therein compared to the paste or paste-like prior art compositions.

The latter adherence characteristics are characterized by the stringy nature of the composition when applied between two surfaces which move away from one another. The Newtonian flow characteristic is important to avoid significant decrease in viscosity upon application of shear forces, such as encountered during use. Also preferred compositions exhibit resistance to melting during use which tends to increase spin off and spattering during use and to cause the composition to flow off the work surface. In either case relatively expensive abrasive particles become unavailable to do work and are wasted or the time required to obtain the desired finish is extended.

It has also been found that not all water soluble gum and seaweed extract combinations provide a semi-gel or sol mixture which possesses the aforementioned desirable properties. Further, it is important in compositions according to the present invention that the water content be significantly lower than taught or typically used in prior art polishing compositions. In compositions according to the present invention, water is preferably below about 10 percent by weight. About 1 to 7 percent by weight of water provides the better properties employing the preferred mixture of gelling agents.

A mixture of gum tragacanth and agar provide the preferred combination of gelling agents in a ratio of about 1 to 40 parts agar to 1 to 40 parts gum tragacanth. The preferred compositions employ this combination of gelling agents in ratios of about 0.75 to 2 parts by weight agar to about 0.75 to 2 parts by weight gum tragacanth. In the more preferred compositions, these ratios are about 1 to 1.5 parts agar to about 0.90 to 1.2 parts gum tragacanth.

In particular, it has been found that the preferred semi-gel or sol compositions of the present invention provide significantly improved polishing results on composite tooth restoration materials compared to the prior art pastes, which results were confirmed by microscopic examination. Although prior art, commercially available diamond polishing compositions exhibited some utility with brush and felt wheel applicators, marked improvements were noted using preferred compositions of the present invention when applied with these types of applicator instruments.

OBJECTS

Therefore it is an object of the present invention to provide a semi-gel or sol composition carrying dispersed abrasive particles which provides improved polishing action and greater efficiency of use of the diamond abrasives.

It is another object of the present invention to provide a polishing composition employing ingredients which are readily usable for human oral applications for polishing teeth and tooth restoration materials in "chairside applications" as well as being useful in laboratory and industrial applications.

It is another object of the present invention, to provide a diamond polishing composition of the type described wherein a semi-gel or sol possesses physical properties which lend themselves to facile dispensing by the user via syringe, single-unit dose packages or other types of convenient dispensing packaging.

It is another object of the present invention to provide a polishing composition of the type described wherein the carrier agent exhibits Newtonian or near Newtonian flow characteristics.

It is a further object of the present invention to provide a semi-gel or sol type polishing composition which exhibits significantly improved physical properties related to adherence to the applicator and the work surface while also tending to adhere to itself to reduce spin off during use and to promote for effective use of the abrasive particle by allowing the particle to remain in effective contact with the work surface for a longer time.

DETAILED DESCRIPTION

The present invention relates to a semi-gel or relatively viscous sol type polishing composition particularly well-suited for carrying small diamond or similar hard abrasive particles for use in producing very fine, mirror-like surfaces. The ingredients of the carrier agent portion include a humectant, preferably glycerine, as a primary liquid vehicle in amounts greater than about 85 percent by weight of the composition. Glycerine functions as a lubricant and a preservative particularly useful with gum tragacanth, one of the preferred gelling agents.

A mixture of solid gelling agents, preferably gum tragacanth and agar, are employed in the liquid portion of the carrier vehicle in a ratio of about 1 to 40 parts agar to 1 to 40 parts of gum tragacanth. A more preferred ratio is about 0.75 to 2 agar to 0.75 to 2 gum tragacanth. A particularly preferred ratio of the gelling agents is about 1 to 1.5 agar to 0.9 to 1.2 gum tragacanth. The most preferred ratios include a slightly greater amount of agar compared to gum tragacanth. The total amount of the gelling agent mixture in the composition of the carrier is preferably in the range of about 1.5 to 4.5 percent with the more preferred range being about 2.1 to 3 percent.

In addition, it is very important to maintain a relatively low amount of water in the composition. Preferably the percentage of water is between about one-half to about 3 times the total weight percent of the mixture of gelling agents. The more preferred compositions of the carrier vehicle include water in the range of about 1 and one-half to 6 percent by weight. If the water content is significantly increased above about 10 percent using the more preferred ratios and total amount of the gelling agent mixture, such compositions exhibit significantly reduced polishing properties for the intended polishing applications. Further, a lower water content is helpful in tending to resist bacterial growth in the composition for bacteria which require a higher water content to exist or multiply. Since certain bacteria can attack the gel composition itself, bacterial growth is undesirable for dental as well as industrial applications.

In the preferred compositions of the present invention useful for dental applications, including performing interoral polishing techniques on a patient in the dentist's chair, the ingredients must be non-toxic, meeting or exceeding U.S.P. grade materials. The gelling agents include an edible gum and a seaweed extract, both of which are food quality and have been used in a variety of food applications. All of the above ingredients are readily available in U.S. P. grade.

An effective amount of recommended and well-known preservatives are included in the composition of the present invention, such as methyl paraben and propyl paraben. These preservatives are soluble in glycerine and other equivalent humectants. Methyl and propyl paraben are added in the present invention in typical effective amounts of about 0.2 and 0.1 weight percent respectively.

Gum tragacanth is a relatively well-known water soluble, edible gum and has been used in prior dental paste and cream formulations, such as disclosed in the prior U.S. patents referred to in the background portion of this application. It has typically been used alone as a gelling agent to stabilize the solid abrasive substance in the liquid vehicle components. Additionally the prior art suggests that other gums provide similar equivalent gelling properties.

However, in accordance with the present invention it has been found that gum tragacanth, when combined with the seaweed extract agar or its equivalent, provide the more preferred physical properties which significantly improve polishing compositions as referred to herein. It has also been found that not all gums or gum-like materials are equivalent to gum tragacanth in providing the unique properties which are desirable in diamond or equivalent type abrasive polishing compositions suitable for applications using relatively high speed rotary applicators under the relatively vigorous conditions required to obtain high grade abrasive polishing action. For example, gum arabic, guar gum, gum karaya and algin were used in various combinations with glycerine and water. The gels formed exhibited one or more physical properties less desirable than those of the preferred compositions disclosed herein, such as greater tendency to spin off, or less effective polishing action, or in certain cases, less than satisfactory shelf life.

Some of these less preferred gums mentioned herein were combined with each other or seaweed extracts and exhibited significantly poorer polishing results and/or tended to exhibit significantly less adherence to the applicator and work surface. In most of these cases, satisfactory shelf life also appeared to be a significant problem which would detract from their commercial acceptance.

Agar is a commonly known edible, seaweed extract whose structure is not completely known. It is considered to be a non-sulfated linear molecule composed of alternating residues of 1,3, beta D-galactopyranose and 1,4-3,6 anhydro -alpha-L galoctopyranose together with a non-gelling or very weak gelling agaropectin composed of a complicated acidic polymer containing ester sulfate groups and organic acid groups.

Other seaweed extracts in the form of commercially prepared propylene glycol alginate, algins or certain carrageenans can be substituted for agar. However tests using such substitute compositions, particularly for the dental polishing applications referred to herein, indicated less desirable results relative to one or more of the most desirable properties obtained using agar. In some instances, the polishing properties are fair to good, but the adherence to the applicator or the work surface is not as excellent as agar-containing compositions. In other instances, the semi-gels or sol formed appear to be too stiff or too thin which significantly detracts from the desired physical properties necessary for improved performance and efficiency of use as earlier discussed herein. However, even some of these less preferred compositions exhibited a degree of positive improvement over the conventional diamond paste or cream type polishing compositions presently available for use in dental applications, even if not as significantly improved compared to the more preferred compositions.

Reference to compositions being "stiff" reflect a gel which is relatively firm with little or no flow deformation upon standing whereas the adjective "thin" reflects a gel or sol which flows readily and does not tend to retain its shape when disposed in a free, unsupported configuration. The preferred compositions of the present invention do exhibit a flow characteristic, but flow slowly upon standing in an unsupported relationship over a given time. The more preferred compositions do not flow so easily as to immediately or quickly deform from an unsupported shape.

With respect to all of the above mentioned gelling agent mixtures and particularly to the gum tragacanth and agar mixtures, it is important that the water content remain at a relatively low level compared to prior art dental polishing compositions. The most desirable compositions contain less than about 10 percent by weight of water with the most preferred containing between about 1 to 7.0 percent water. Test results revealed that as the water content approached 10 percent or higher, the results regarding polishing effectiveness were not as good as for those compositions containing between 1 to 7 percent water.

Further, it was found that the total amount of the gelling agent mixture effects the desired properties of the final composition. A total approaching about 4.4 to 5 percent by weight of the mixture of the gelling agents tends to make the composition too viscous and/or gelatinous for the intended purpose. Such compositions are difficult to apply to the applicator. Additionally, the choice of packaging such compositions is significantly reduced as they are not easily loaded into or dispensed from a syringe type applicator and not sufficiently workable to permit convenient manufacture of packaging in squeezable dispensing tubes or individual dose packets.

Conversely, there must be a sufficient amount of the gelling agent mixture to form the semi-gel or sol having the desirable properties described herein according to the present inventions. While an absolute lower limit has not been established, about 1.5 to 2.5 weight percent of the mixture of gelling agents provides operable compositions having the desirable properties referred to herein. The more preferred total amount of the mixture of gelling agents in the ratio referred to herein is about 1.9 to 2.2 weight percent of the total carrier composition.

It should be noted that the weight percentages mentioned herein are on the basis of the total weight of the carrier vehicle including a small percentage of preservatives and exclude the weight of the diamond particles or other equivalent abrasive polishing agents dispersed therein. The amount of abrasive particles added can vary depending upon the application and the type of abrasive used. For most applications, about 0.5 to 1.0 carat of diamond particles per gram of the vehicle carrier provides excellent polishing results. The specific amount and particle size of the abrasive may vary depending upon the nature of the surface finish desired. However, it has been found that about 0.5 carat of diamond particles work very well in dental applications which is about one-half of the amount used in many presently marketed dental diamond polishing compositions. Such a reduction in the amount of abrasive material employed while still achieving the improved polishing action indicated in the tests results to date further evidences the improved properties of the carrier vehicle included in polishing compositions of the present invention. It is believed these properties improve the degree to which the dispersed abrasive particles are maintained in a more effective relationship with the rotating applicator and the work surface to enhance performance.

Other well-known abrasive materials would be expected to work well in accordance with the present invention in industrial applications and would be chosen according to the nature of the work surface and the type or nature of the work to be performed.

In the dental field for example, substituting zirconium silicate for diamond provides a good composition for typical tooth cleaning applications normally done in routine dental visits. The attributes of the carrier vehicle described herein are also applicable in this particular application wherein a rotary dental applicator is used to primarily clean tooth or tooth restorative surfaces. Such compositions are commonly known as "prophy pastes".

The following specific examples are given to illustrate the present invention further, but it is understood that the invention is not limited thereto. Each of the following formulations illustrate laboratory batch sizes which could be appropriately proportionally increased for production size batches. The following steps illustrate the method of making compositions according to the present invention set forth in the examples.

Glycerine, or other humectants are added to the mixing vessel first. At room temperature, the preservatives methyl paraben and propyl paraben are added in small portions while stirring, and the components are heated to between 180-200 degrees F. with continued stirring until the preservatives are completely dissolved in the glycerine. Water and the gelling agents, agar and gum tragacanth are then added in small portions into the solution with rapid stirring while the temperature is maintained between 180-200 degrees F.

With continued stirring, the mixture is heated further to a temperature between about 212 to 220 degrees F. Stirring is continued for between 45 to 70 minutes as necessary to allow for maximum dispersion of the gelling agent mixture. It is desirable to minimize the entrapment of air bubbles while adding the gelling agents. The time the solution is maintained at the maximum temperature range should not exceed 70 minutes and temperatures should not exceed about 220 degrees F. to avoid excessive darkening of the mixture. After completion of the above heating cycle, the mixture should be strained through a number 20 mesh sieve (U.S. sieve size), or an equivalent, if any visible undispersed particles of the solid gelling agents are present. With appropriate care in adding the gelling agents, the amount of such visible particles is usually insignificant relative to the proportions added.

After the heating cycle has been completed, the temperature of the mixture should be adjusted to between 180-200 degrees F. and the diamond o other abrasives particles added in small portions with mixing until completely homogeneously dispersed throughout the mixture.

For production runs, the mixture is then ready for filling into the chosen dispenser, such as for example, a typical 2 gram plastic syringe type commonly employed for diamond polishing pastes. Upon cooling to room temperature, the composition sets up to the viscous, semi-gel or sol such as described earlier herein.

EXAMPLE I

A carrier vehicle was prepared according to the present invention having the following composition:

|  | Weight in grams | Weight Percent |
| --- | --- | --- |
| Glycerin, U.S.P. | 114.3896 | 96.31 |
| Methyl paraben | 0.2288 | 0.19 |
| Propyl paraben | 0.1144 | 0.10 |
| Agar, powder 150 mesh, U.S.P | 1.3080 | 1.10 |
| Gum tragacanth, U.S.P. | 1.1913 | 1.00 |
| Distilled Water | 1.5417 | 1.30 |
|  |  | 100.00 |

The mixture of the above components was prepared as described above herein and allowed to sit overnight. A semi-gel or sol was formed having a somewhat sticky and stringy nature which was evidenced dramatically when applied between two surfaces which were then drawn apart. The composition formed tends to draw out in a plurality of strands with significant amounts remaining on the opposing surfaces upon drawing the surfaces away from one another. This illustrates its tendency to adhere to the surfaces contacted as well as to itself. The composition was tested by placing a small portion on a conventional rotary applicator inserted into a conventional low speed dental hand piece operated at about 6000 to 7000 rpm on various tooth restorative materials. These materials included porcelain and those referred to in the trade as microfil, macrofil and hybrid composites. Microscopic investigation showed excellent polishing effectiveness. Very little, if any, significant spin off of the polishing composition was noted during the polishing step. No liquefying or other significant decrease in viscosity of the composition was apparent during the polishing step which was conducted in 15 to 30 second time intervals.

It is important to note that it is necessary to apply only a relatively small portion of the composition to the applicator to achieve good results. It is obviously apparent that if a significant excess is applied, spin off and initial spatter increases, however this is simply poor technique evident to any skilled user of compositions for these applications.

It is also important to note that in this and the following examples, the prior surface condition of the surface being polished was prepared in the same manner. Such preparation included using commercially available micron sized diamond dental burs or diamond coated strips, such as those sold by Abrasive Technology, Inc. under the trademarks "MFS" Diamonds and "COMPO-STRIP" Other similar commercially available products could be used for final contouring of tooth surfaces. Such tools typically employ diamond particles in the 10 to 50 micron range.

Further, it should be noted that the comparative testing referred to herein using presently commercially available prior art dental diamond polishing compositions also included this same pre-conditioning step of the work surface.

The testing of compositions of the present invention also included using different forms of conventionally used and accepted rotary actuators. These included, the bristle brush, rubber prophy cup, and felt wheel. A new small conical nylon tip designed for access to otherwise difficult to reach tooth surfaces was also used. While a difference in performance was noted between the various applicators, (the bristle brush type appeared best for all compositions tested) the preferred compositions of the present invention consistently were markedly improved in resisting spin off and spatter and generally provided improved polishing effectiveness compared to prior art commercially available diamond polishing compositions. This is particularly noteworthy as some prior art compositions tested included twice the amount of diamond abrasive particles per gram of the composition compared to the tested compositions of the present invention. The improved polishing effectiveness is attributed in part to the ability of compositions of the present invention to cling better to the applicator and the work surface with no apparent significant decrease in viscosity due to shear forces or increased temperatures, as well as to a reduction in the loss of the composition by spinning off during use.

Further, it was noted that during the testing using some restorative tooth materials, particularly the hybrid and microfil composite types, sequenced two-step polishing steps obtained a very dramatically improved finished surface. These steps include using extra fine diamond dental burs for final contouring and preferably diamond coated strips for access to difficult small areas. A two-step sequence includes first polishing the surface using a composition of the present invention having five micron diamond particles for 15 to 30 seconds. This is then followed with a second similar step of polishing with the same composition, except 0.25 micron diamonds are substituted for the 5 micron size particles in the carrier vehicle.

The reference to 0.25 micron particles is defined as particles which are presumed to average 0.25 microns and may include particles in the size range of 0 to 0.5 microns. Similarly, the other micron sizes are used in a conventional sense known in the industry to specify the average particle size covering the range obtained using standard methods of size separation.

For some tooth restoration materials, a three step procedure appears most useful to achieve the best results utilizing carrier vehicles according to the present invention having 9 micron diamond in first polishing step, followed by a composition containing 1 micron diamond particles and lastly a composition containing 0.25 micron diamond particles.

Compared to commercially available diamond polishing compositions using nominally labeled 3 micron diamond in a single step, tests to date show the graded size, multiple step procedure disclosed herein provided a truly superior finish on composite restorative tooth materials unachieved in the past.

Microscopic investigation has revealed that the prior art dental diamond compositions often fail to satisfactorily remove prior surface treatment scratches and tend to do no more than smooth the larger surface deviations leaving microscopic scratches in which dental plaque tends to more easily accumulate. The improvement in surface lustre is only fair at best, particularly when compared to that achieved utilizing compositions of the present invention. The polishing results using of these prior compositions were significantly inferior compared to multiple sequenced polishing steps as referred to above using compositions according to the present invention.

The preferred vehicle or carrier compositions of the present invention suspend larger particle size particles (such as 9 micron) and the smaller size particles (down to 0.25) very well and are very effective in creating a condition between the applicator and the work surface to promote effective polishing action representing a significant improvement over the prior art compositions in single step applications.

However, combining the increased efficiency and effectiveness of compositions of the present invention with the multiple step polishing sequence, surface finishes which are truly superior and heretofore unachieved have been obtained.

The following table illustrates other carrier vehicle composition examples prepared in a similar manner as in Example I and lists the weight percent of each ingredient except the methyl and propyl paraben preservatives which are added in the same percent as in Example I.

| EXAMPLE | WATER | AGAR | GUM TRAGACANTH | GLYCERINE |
|---|---|---|---|---|
| II | 0 | 4.1 | 0.10 | 95.50 |
| III | 2.6 | 0.1 | 4.10 | 92.90 |
| IV | 2.6 | 4.1 | 0.10 | 92.90 |
| V | 1.04 | 1.11 | 0.57 | 96.98 |
| VI | 1.56 | 0.74 | 0.94 | 96.46 |
| VII | 1.04 | 1.11 | 1.41 | 96.14 |
| VIII | 1.56 | 1.45 | 1.07 | 95.62 |
| IX | 1.3 | 1.1 | 1.0(guar gum) | 96.30 |
| X | 6.0 | 1.1 | 1.0 | 91.60 |
| XI | 10.0 | 1.1 | 1.0 | 87.60 |

Using the compositions listed in Examples II through XI in tests as described in Example I revealed that the more preferred compositions regarding polishing effectiveness, adherence to the applicator and the work surface to resist spin off, as well as ease of manufacture in a convenient dispensing package were Examples I and X with Examples V through VIII rated as good.

Examples II, III and IV were effective in polishing action, although not rated as highly as the above-mentioned more preferred compositions. Further, Examples II through IV tended to be thicker and not as desirable for easy loading into syringe type dispensers or single-dose containers.

Examples IX and XI did not exhibit the desirable physical properties or polishing effectiveness to as high a degree as compared to the more preferred compositions.

Examples I and X were considered the best of all the compositions tested to date. Example X even rated somewhat better than Example I in polishing action, particularly when using the bristle brush type applicator. Initial tests showed Example X appeared to produce the most lustrous, microscopically smoothest surface of all compositions tested.

All of the compositions are readily removed from the applicator and work surface by flushing with water.

Many varieties of combinations of edible, natural gums and seaweed extracts were tested, such as the alginates as a substitute for agar and guar gum as a substitute for gum tragacanth. However, while some of these compositions showed a degree of utility relative to polishing action, the gum tragacanth and agar formulations provided the best results in tests completed to date. Further, some of these other combinations were significantly less effective regarding reducing spin off of the composition during use or resisting decreases in viscosity due to heat or shear forces as compared to the preferred embodiments disclosed herein.

While testing to date was relatively extensive, development of more specific ranges of the various components disclosed may require further test data to obtain a more detailed analysis of the specific physical properties which appear to be the most important regarding enhancing the improved polishing action noted using compositions according to the present invention.

It should also be noted that the comparative testing referred to herein was conducted using prior art commercially available dental diamond polishing compositions having only general label information including identifying diamond particle size as 3 microns. However, the specific components and formulations are apparently proprietary and not identified other than the generic reference to gums or seaweed extracts.

However, the difference in physical properties between these commercially available compositions and those of the present invention are readily apparent even to the untrained eye, particularly relative to the more viscous and adherent nature of the semi-gel or sol formed in the present invention. Further, the elongated strands formed when compositions of the present invention are drawn out is strikingly different compared to the creamy or paste-like consistency of these commercially available compositions.

It should also be noted that the tests referred to herein were evaluated on a qualitative basis of the visual improvement of lustre and microscopic examination of the polished surfaces as well as the visually detectable difference in spin-off or spattering during use of the various compositions tested.

It should also be understood that conventional additives to add color, flavor or possible fluorides in amounts which do not effect the functional properties of the polishing composition may be added thereto without departing from the spirit of the invention.

In view of the forgoing description, it should be understood by those skilled in the art that an improved polishing composition and method is disclosed which is a significant step forward in preparing a superior surface finish for industrial applications in general and particularly as applied in the dental field.

While certain preferred embodiments of the present invention have been disclosed in detail, it is to be understood that various modifications may be adopted without departing from the spirit of the invention or scope of the following claims.

We claim:

1. An abrasive polishing composition comprising an amount of diamond or other equivalent hard abrasive particles effective to remove material from a substrate being polished dispersed in a semi-gel or sol carrier vehicle, said carrier vehicle including:
   a) a humectant selected from the group consisting of glycerine and propylene glycol or mixtures thereof in an amount greater than about 85 percent by weight of the carrier vehicle;
   b) solid gelling components comprising a mixture of gum tragacanth and a seaweed extract selected from a group consisting of agar, carrageenans, algins or mixtures thereof, the ratio between said gum tragacanth to said seaweed extract ranging between 0.75 to 2 parts gum to 0.75 to 2 parts seaweed extract; and
   c) water in an amount less than about 10 percent by weight of said carrier vehicle.

2. The composition defined in claim 1 wherein said solid gelling components are of food grade quality.

3. The composition defined in claim 2 wherein said gum is gum tragacanth.

4. The composition defined in claim 2 wherein the total amount of said gelling components is less than about five percent by weight of the total carrier vehicle formulation.

5. The composition of claim 1 wherein said gelling components are gum tragacanth and agar.

6. The composition defined in claim 5 wherein the ratio of gum tragacanth to agar is about 0.9 to 1.2 parts gum tragacanth to about 1 to 1.5 parts agar.

7. The composition defined in claim 5 wherein said semi-gel or sol has Newtonian or closely approximates Newtonian flow characteristics.

8. The compositions defined in claim 1 wherein said water content is between about 1 to 9 percent by weight of the carrier vehicle composition.

9. The composition defined in claim 1 wherein said semi-gel or sol has Newtonian or closely approximates Newtonian flow characteristics.

10. The composition defined in claim 1 further comprising an effective amount of methyl paraben and propyl paraben as preservatives.

11. The composition defined in claim 1 wherein said semi-gel or sol exhibits resistance to liquification and reduction of viscosity at temperatures generated under normal use conditions.

* * * * *